(12) United States Patent  (10) Patent No.: US 8,365,429 B2
Lawrence et al.  (45) Date of Patent: Feb. 5, 2013

(54) METHOD AND TEMPLATE FOR PRODUCING A TENSILE TEST COUPON

(76) Inventors: Jason A. Lawrence, Owasso, OK (US); James R. Perrault, Tulsa, OK (US); Brian O'Connell, Tulsa, OK (US)

( * ) Notice: Subject to any disclaimer, the term of this patent is extended or adjusted under 35 U.S.C. 154(b) by 486 days.

(21) Appl. No.: 12/564,735

(22) Filed: Sep. 22, 2009

(65) Prior Publication Data

US 2011/0067499 A1    Mar. 24, 2011

(51) Int. Cl.
    *G01B 3/14*    (2006.01)
(52) U.S. Cl. .............................. 33/562; 33/529
(58) Field of Classification Search .................... 73/827; 33/562, 529; 408/72 R
    See application file for complete search history.

(56) References Cited

U.S. PATENT DOCUMENTS

| | | | |
|---|---|---|---|
| 4,574,443 A | 3/1986 | Persak et al. | |
| 6,070,911 A | 6/2000 | Namikawa et al. | |
| 6,510,865 B2 | 1/2003 | King et al. | |
| 6,643,945 B1 | 11/2003 | Starks | |
| 2006/0191445 A1 | 8/2006 | Stengel et al. | |
| 2008/0152442 A1 | 6/2008 | Barrett | |

OTHER PUBLICATIONS

Zhao et al., "Effect of joint contamination on the quality of butt-fused high-density polyethylene (HDPE) pipe joints." NRCC-45337, Canadian Journal of Civil Engineering.
International Search Report and Written Opinion issued by the International Searching Authority (ISA/US) on Nov. 19, 2010 in PCT/US10/49621.

*Primary Examiner* — Lisa Caputo
*Assistant Examiner* — Jonathan Dunlap
(74) *Attorney, Agent, or Firm* — Gable Gotwals

(57) ABSTRACT

A method and template enable the testing of fusion joints of plastic pipes to be conducted by a single operator in the field at the welding site by the efficient and precise extraction from the joints to be tested of a number of high quality tensile coupons. The coupons are tested to failure in a field-suitable, well controlled, self contained, tensile testing apparatus. A narrowing bow-tie-like pattern of the coupon ensures that the failure of the coupon in the tensile test will occur at the narrowest section of the coupon. The template can be visually aligned with the joint to ensure that it is the joint that will be tested.

20 Claims, 5 Drawing Sheets

Fig. 6
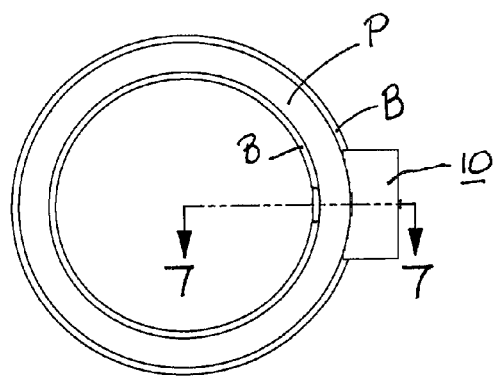
Fig. 7
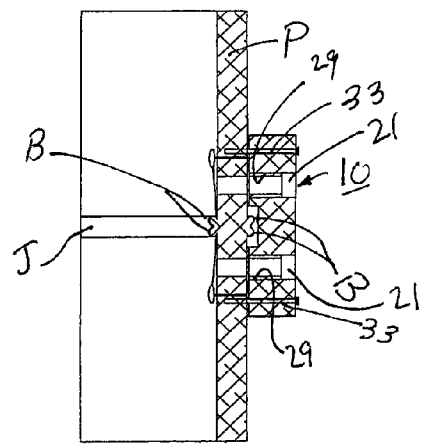
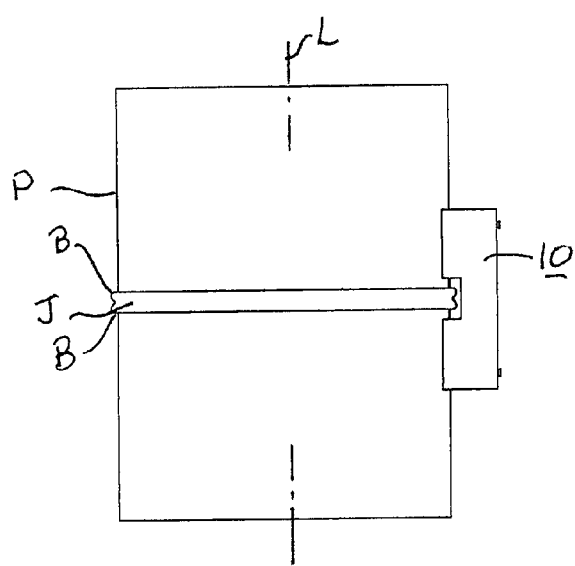
Fig. 8
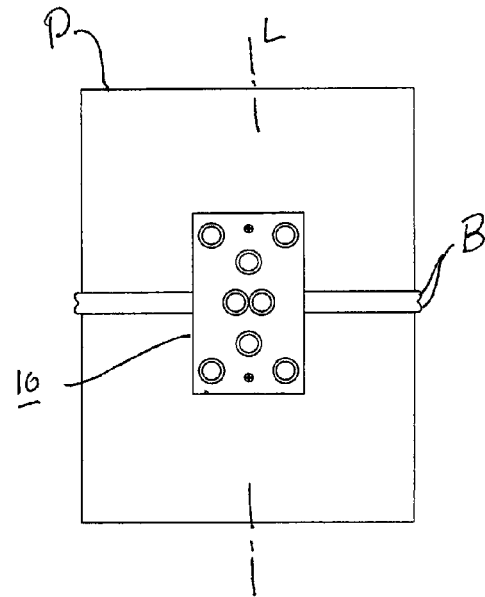
Fig. 9

Fig. 14
Fig. 15
Fig. 13
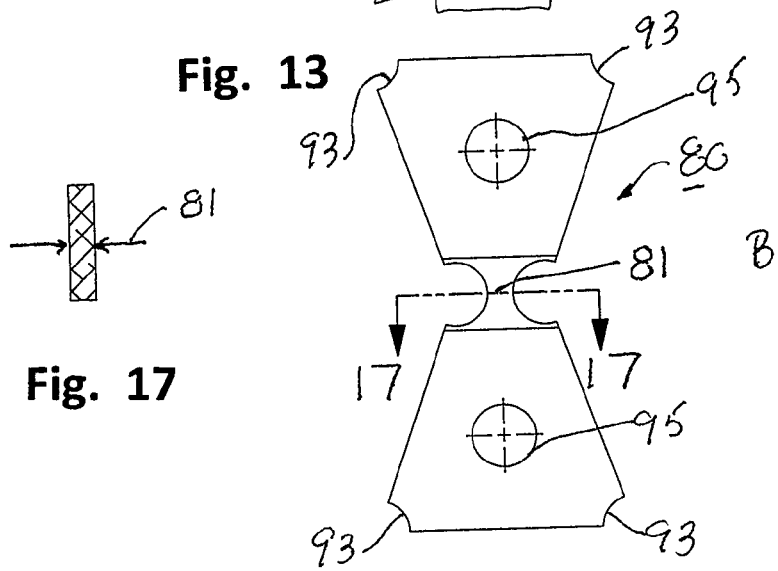
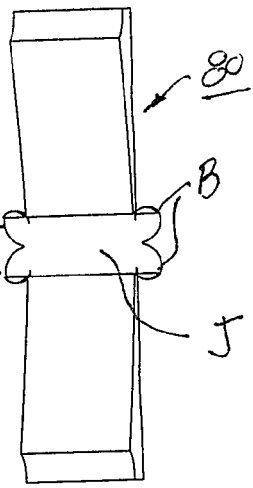
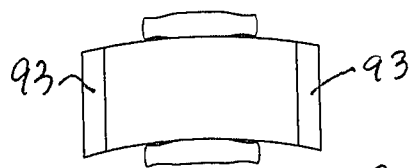
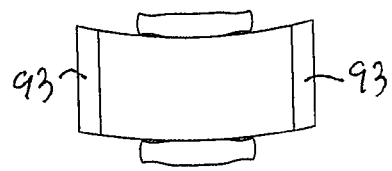
Fig. 17
Fig. 16

METHOD AND TEMPLATE FOR PRODUCING A TENSILE TEST COUPON

BACKGROUND OF THE INVENTION

This invention relates generally to the quality testing of heat-fused plastic pipe joints and more particularly concerns a method and template for producing a coupon which can be used to test the properties, such as the tensile strength and ductility, of a pipe joint as the pipe is being laid in the field.

Plastic pipes, such as pipes made of medium or high density polyethylene, can be joined by a variety of methods, a common joining method being butt-fusion. The procedure for this method involves inserting pipes to be fused into a specially designed fusion machine which aligns and holds the pipes axially with respect to each other and with pipe ends adjacent to each other, clamping the pipes securely in the jaws of the fusion machine, cleaning of the pipe ends to be fused, facing the pipe ends to ensure clean and square pipe ends with material exposed that is suitable for heat fusion, heating the pipe ends for an appropriate amount of time, and then joining the heated pipe ends under pressure and allowing the fused pipes to cool.

The integrity and usefulness of the pipeline requires quality fused joints with acceptable mechanical performance qualities. Therefore, tensile test methods have been devised which are intended to assure that a pipeline is being constructed of such quality as can reasonably be expected to pass final testing of the pipeline for use as designed. Unfortunately, most of these tensile test methods now available require instrumentation and apparatus which are not suited for field use. Their tensile test coupons are used in laboratory test methods and are typically produced on non-portable machine tools.

A few destructive field-testing methods have been devised for checking the mechanical performance of the fused joint during pipeline production. The most common in-production tensile test method is the "bend back" test. In the "bend back" test, a strap of material is extracted from a fused joint and its adjacent sections of pipe. The extracted strap is bent in such a direction that the maximum tensile and compressive bending stresses are applied to the portions of the strap that originated on the outer and inner diameters of the pipe. According to this test, a "good" joint is one which shows good bond integrity after bending. The straps are typically air bent, if practical, but if more force is needed to bend the strap to the degree required, implements may be applied.

The required length of the "bend back" strap may vary and, for greater pipe wall thicknesses, the forces required to bend the strap become high, containment in the case of failure becomes more difficult and the method becomes safety and cost prohibitive. In addition, the levels of stress imposed upon the fused joint are heavily dependent on uncontrolled or unknown factors such as the bend radius and the types of tooling used to bend the strap. These variables result in uncertainty as to the significance of any passing grade resulting from this test. Furthermore, for larger pipe diameters which require longer straps of pipe for testing, the material cost for the strap of pipe required to apply an appropriate bend test load can be quite expensive.

It is, therefore, an object of this invention to provide a method and template which facilitate the efficient and precise extraction of high quality tensile test coupons from a fused joint. Another object of this invention is to provide a method and template which facilitate speedy field evaluation of the quality of a fusion joint. A further object of this invention is to provide a method and template which ensures that the failure of the coupon in the tensile test will occur at the joint. It is also an object of this invention to provide a method and template which produce tensile test results which are qualitatively comparable to both/either a sample made from the pipe material and/or against predetermined qualitative criteria for acceptability. Still another object of this invention is to provide a method and template which require extraction of less pipe material for destructive tests than the "bend back" test.

SUMMARY OF THE INVENTION

In accordance with the invention, a method is provided for producing a tensile test coupon from a plastic pipe. The method includes the step of drilling an array of holes through a wall of the pipe. The drilled array defines a straight-line-connectable point-to-point pattern for the coupon. The method also includes the step of making straight line cuts with a reciprocating saw. The cuts connect the array of holes in the pattern of the coupon, thus separating the coupon from the pipe.

The holes of the coupon-defining array are arranged symmetrically in relation to a pair of intersecting axes, one axis being tangential to and the other axis being longitudinal along, an outer surface of the pipe. Preferably, the holes of the coupon-defining array define a bow-tie-like coupon symmetrical with respect to the tangential and longitudinal axes and the tangential axis lies in the plane of the interface between the fused sections of the pipe.

The method may also include the step of laying a template on the outer surface of the pipe. An array of holes through the template defines the straight-line-connectable point-to-point pattern for the coupon. With the template so positioned on the pipe, in the next step the template holes are used to guide the drilling of the array of pattern holes through the pipe. Thereafter, the method includes the step of removing the template from the pipe before making the straight line cuts.

The method may also include the additional step of drilling at least two more additional holes through the wall of the pipe and within the pattern of the coupon before cutting the coupon. These additional holes are oriented to facilitate application of tensile force to the extracted coupon along the narrowest cross-section of the coupon.

The template for use in producing a tensile test coupon from a plastic pipe has a plate contoured for stable abutment on the outer surface of the pipe. For example, the contour may be a V-groove aligning the longitudinal axis of the plate with the longitudinal axis of the pipe. An array of holes through the plate defines a straight-line-connectable point-to-point pattern for the coupon. At least two additional holes through the plate and within the pattern of the coupon are oriented to facilitate application of test tensile force to the extracted coupon at the narrowest cross-section of the coupon. The holes of the coupon-defining array may be arranged for symmetrical orientation in relation to a pair of intersecting axes, one axis being tangential to and the other axis being longitudinal along, the outer surface of the pipe when the plate is in stable abutment on the pipe. The symmetrical orientation of the array enables production of a symmetrical coupon. The at least two additional holes may be arranged for symmetrical orientation straddling the tangential axis and along the longitudinal axis. The symmetrical orientation of these holes, in cooperation with the symmetry of the coupon, allows the test tensile force to be symmetrically applied to the coupon. The plate is provided with a relief to receive beads formed on the outer surface of the pipe by fusion of the pipe along its plane of fusion interface. The tangential axis lies in the plane of interface so the plate can be in stable abutment on the pipe even though the outer diameter of the joint at the beads is greater than the outer diameter of the pipe. The holes of the coupon-defining array and the additional symmetrical holes may each be fitted with a hardened drill bushing.

Any of the above methods may further preferably include the step of securing the template to the outer surface of the pipe before drilling. For example, if at least two additional holes are provided through the template, the step of securing may be accomplished by driving screws which are inserted through the additional holes into the pipe.

BRIEF DESCRIPTION OF THE DRAWINGS

Other objects and advantages of the invention will become apparent upon reading the following detailed description and upon reference to the drawings in which:

FIG. 6 is an end view of the tensile test coupon template of FIG. 1 mounted on a pipe;

FIG. 7 is cross-sectional view taken along the line 7-7 of FIG. 6;

FIG. 8 is a side elevation view of the tensile test coupon template of FIG. 1 mounted on a pipe;

FIG. 9 is a plan view of the top of the tensile test coupon template of FIG. 1 mounted on a pipe;

FIG. 13 is a top plan view of a coupon extracted from a pipe;

FIG. 14 is an end of the coupon of FIG. 13;

FIG. 15 is a side elevation view of the coupon of FIG. 13;

FIG. 16 is another end view of the coupon of FIG. 13; and

FIG. 17 is cross-sectional view taken along the line 17-17 of FIG. 13.

Figure 1:
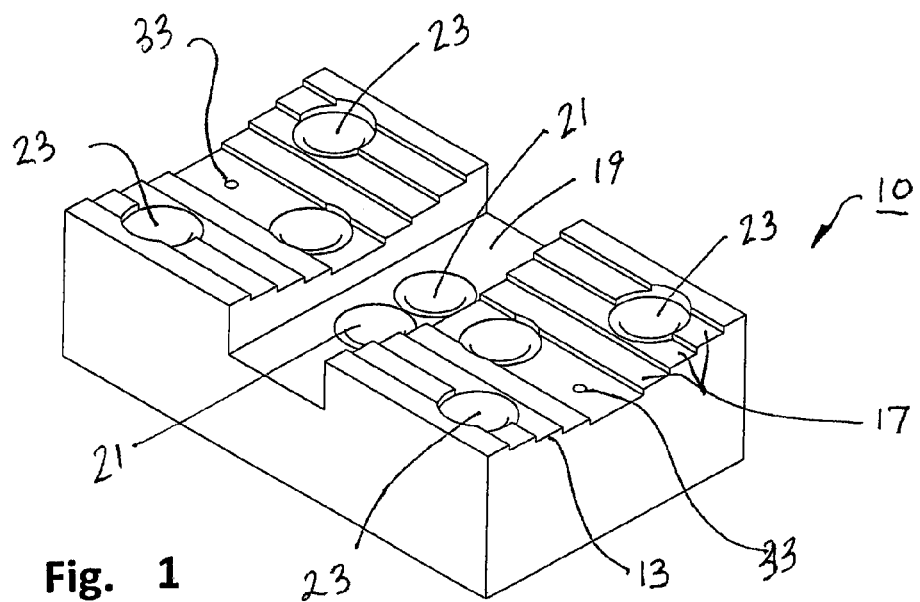
FIG. 1 is a perspective view of a preferred embodiment of the tensile test coupon template.
Figure 2:
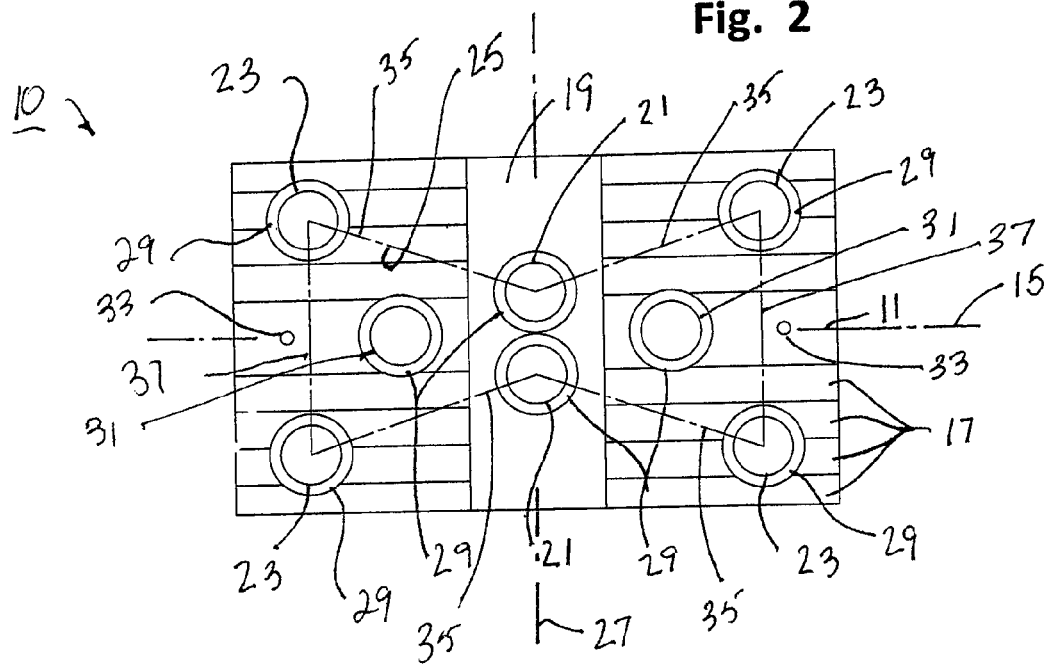
FIG. 2 is a plan view of the base of the template of FIG. 1.
Figure 3:
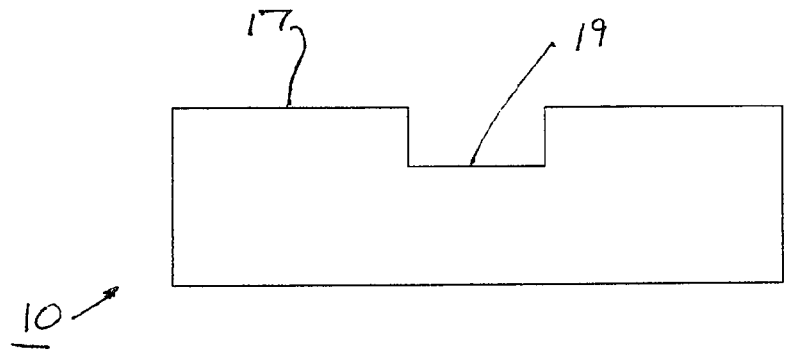
FIG. 3 is a side elevation view of the tensile test coupon template of FIG. 1.
Figure 4:
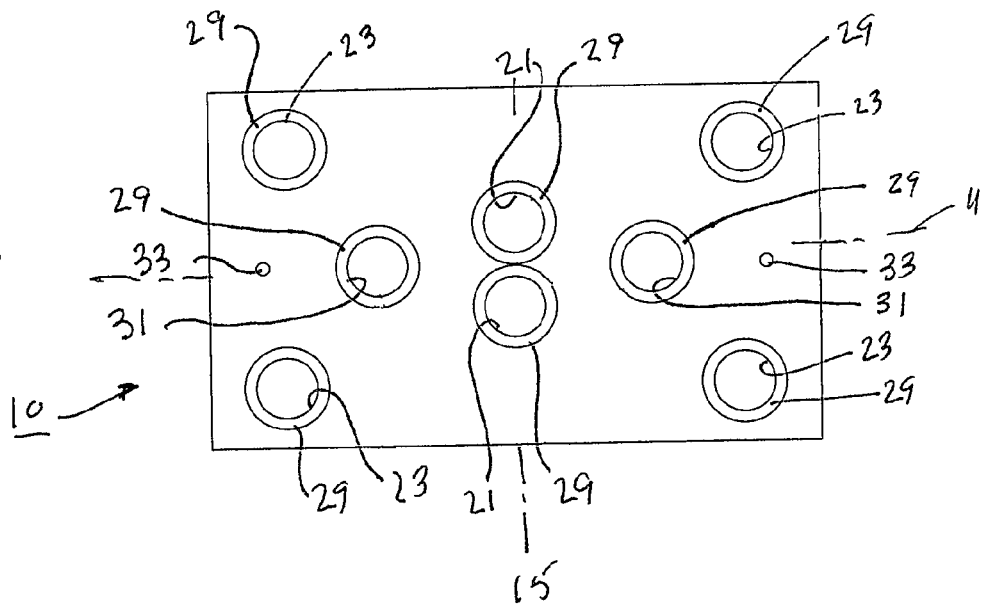
FIG. 4 is a plan view of the top of the tensile test coupon template of FIG. 1.
Figure 5:
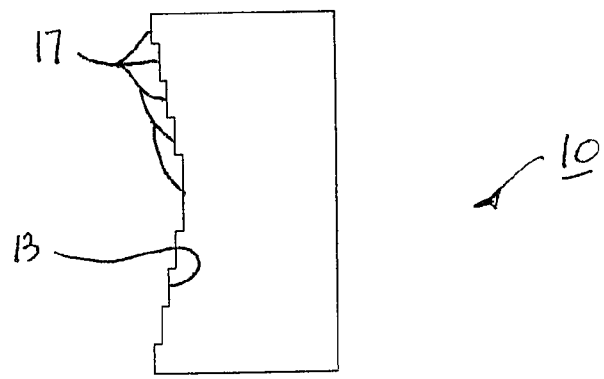
FIG. 5 is an end view of the tensile test coupon template of FIG. 1.
Figure 11:
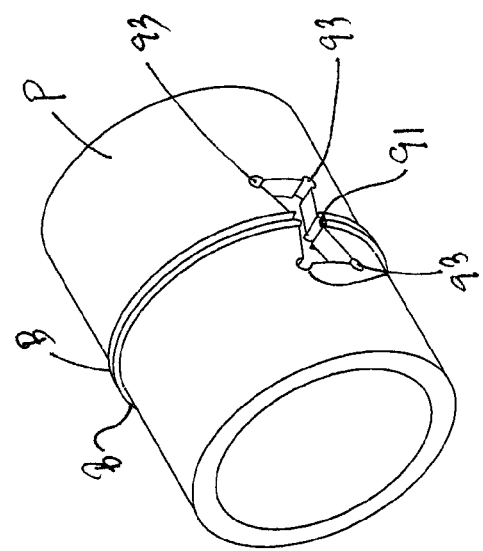
FIG. 11 is a perspective view illustrating another step of the method of using the tensile test coupon template of FIG. 1.
Figure 12:
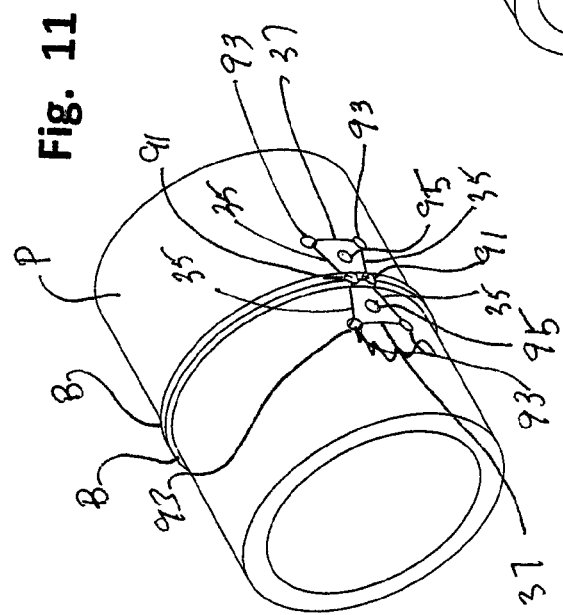
FIG. 12 is a perspective view illustrating yet another step of the method of using the tensile test coupon template of FIG. 1.
Figure 10:
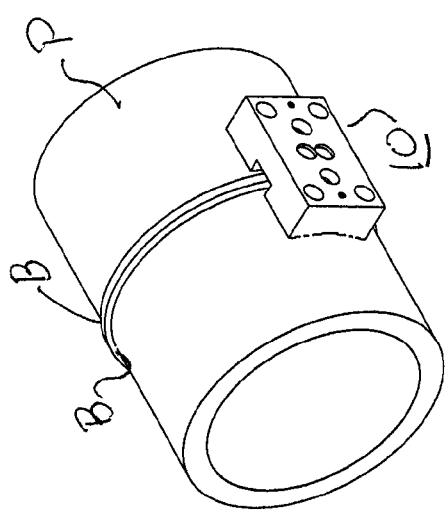
FIG. 10 is a perspective view illustrating a step of the method of using the tensile test coupon template of FIG. 1.

While the invention will be described in connection with a preferred embodiment thereof, it will be understood that it is not intended to limit the invention to that embodiment or to the details of the construction or arrangement of parts illustrated in the accompanying drawings.

DETAILED DESCRIPTION

The Template

Turning to Figures, a preferred embodiment of a template 10 for producing a tensile test coupon 80 from a plastic pipe P or a fused joint J of a plastic pipe P is illustrated. The template 10 is useful over a broad range of pipe diameters and compositions, but is particularly applicable for medium or high density polyethylene pipes.

The template 10 is formed using a relatively thick plate of material such as commercially available aluminum or steel suited for machining. The template 10 has a base 11 which, in using the template 10, will be abutted against the outer surface of the pipe P. The contour of the base 11 can take many shapes so long as the template 10 is stable in its alignment when held against a pipe P.

As shown, the base 11 has a V-groove 13 which, in cross-section, is transverse to the longitudinal axis 15 of the template 10. Thus, the pipe and template longitudinal axes L and 15 will be parallel when the template 10 is abutted in its stable condition against the pipe P. As shown, the V-groove 13 has a stepped pipe-contacting surface 17 which allows the template 10 to center on the curvature of the pipe P. The steps 17 can be configured to further stabilize the template 10 on the pipe P by reason of their gripping effect or to allow use of the same template 10 with pipes P of different diameters.

A relief 19 in the base 11 extends perpendicular to the longitudinal axis 15 of the template 10. The relief 19 allows the template 10 to be centered over the beads B of a fusion joint J but does not prevent attachment of the template 10 anywhere along the pipe P regardless of the presence of a fusion joint J.

The template 10 has an array of holes 21 and 23 through it which define a pattern 25 in the template 10 in the desired shape of the tensile test coupon 80. These holes 21 and 23 are starting and ending points for saw cuts by a reciprocating saw. As shown, the holes 21 and 23 are arrayed to define a straight-line-connectable point-to-point pattern 25, considering the center of each hole 21 and 23 as the point of definition. The pattern 25 shown has a bow-tie-like shape which is symmetric in relation to the longitudinal 15 and relief 27 axes of the template 10. As shown, four holes 23 of the array allow the operator to form the outer "corners" of the coupon 80 and two holes 21 of the array allow the operator to connect the "corners" to the narrowest cross-section 81 of the bow-tie-like coupon 80. As shown, the narrowest-cross-section holes 21 are aligned at the center of the bow-tie-like pattern. As shown, each hole 21 and 23 of the array is fitted with a hardened drill bushing 29 which will precisely guide a drill bit driven by a hand drill. The drill bushings 29 ensure that the holes 21 and 23 produced during drilling will be parallel to each other to a close degree of precision and reduce wear on the template 10.

Additional holes 31, as shown two holes 31 with the same diameters as the holes 21 and 23 of the coupon array, extend through the template 10 within the confines of the pattern 25. The additional holes 31 will be used in a pin and clevis arrangement associated with a tensile testing device for application of tensile force to the coupon 80. In the two additional hole configuration shown, the holes 31 are centered on the longitudinal axis 11 of the pattern and symmetrically straddle the relief axis 27 so that the tensile force will be evenly applied at the narrow cross-section 81 of the coupon 80. As shown, the additional holes 31 are also each fitted with a hardened drill bushing 29.

In use, it is preferred that the template 10 be temporarily affixed to the pipe P. As shown, this is accomplished by use of mounting holes 33, as shown two holes 33 which extend through the template 10, symmetrically straddling the relief 19 and aligned on the longitudinal centerline 15 of the template 10. Coarsely threaded wood screws can be driven through the holes 19 into the pipe P to temporarily secure the template 10 in place. As shown, the mounting holes 33 are outside of the confines of the coupon pattern 25. However, the exact placement and number of the mounting holes 33 is not critical. The holes 33 need only serve as pilot holes for the wood screws which are driven into the pipe P to hold the template 10 firmly against the pipe P and anchor the template 10 while the coupon pattern 21 and 23 and tensile force 31 holes are drilled.

The Method

The method for producing a tensile test coupon 80 from a plastic pipe P involves the steps of drilling an array of holes 21 and 23 through the wall of the pipe P to define a straight-line-connectable point-to-point pattern 25 for the coupon 80, drilling at least two additional holes 31 through the wall of the pipe P within the pattern 25 of the coupon 80 for facilitating application of tensile force to the coupon 80 at its narrowest cross-section 81 and making straight line cuts 35 and 37 with a reciprocating saw, the cuts 35 and 37 connecting the array of holes 21 and 23 in the pattern 25 of the coupon 80 to separate the coupon 80 from the pipe P.

Using the template 10 of the present invention, the method can be applied with speed and accuracy in the field. At the geographic location of the fusion process, the method involves the steps of laying the template 10 on the outer surface of the pipe P, using the template holes 21, 23 and 31 to guide the drilling of an array of coupon holes 91, 93 and additional holes 95 through the pipe P and removing the template 10 from the pipe P before making the cuts 35 and 37 to connect the pattern holes 91 and 93 in the coupon 80. Before drilling, the template 10 can be secured to the outer surface of the pipe P, as by driving screws through the template mounting holes 33.

In the laying step, the V-groove 13 aligns the template 10 and pipe longitudinal axes L and, if the coupon 80 is to be taken at a fusion joint J of the pipe P, the template holes 21 at the narrowest cross-section 81 of the coupon 80 are visually aligned on the plane of the fusion interface between the fusion beads B which lie in the relief 19 on the template 10. In the securing step, a screwdriver can be used to install coarsely threaded wood screws through the mounting holes 33 of the template 10 into the pipe P to be tested. The screws firmly, but temporarily, attach the template 10 to the outer surface of the pipe P. A hand drill with a bit of appropriate diameter to accommodate the width of a reciprocating saw blade is used to drill the coupon pattern 21 and 23 and tensile force 31 holes. A twist drill bit of diameter and length of flute to evacuate the drilled pipe chips and shavings out the upper side of the template 10 when fully engaged with the pipe P is preferred for drilling through the holes 21, 23 and 31 and the pipe P. The template guides the bit through the hardened drill bushings and into and through the wall of the pipe P. The screwdriver is again used to unthread the wood screws from the pipe P and remove the template 10. A hand held reciprocating saw can be used to make cuts 35 and 37 which connect the outer or coupon pattern holes 91 and 93 in the pipe P, leaving the pin and clevis holes 95 within the confines of the coupon 80 intact and separating the coupon 80 to be tested from the pipe P. Preferably, the saw cuts 35 are made in the pipe P from the center holes 91 to the corner holes 95 and then two final cuts 37 are made from corner hole 95 to corner hole 95 parallel to the plane of fusion between the beads B, the final cuts 37 freeing the coupon 80 from the pipe P. The coupon 80 is ready to be loaded into an on on-site tensile testing device such as a manually pumped, hydraulically actuated tensile testing machine, suitable for field use by a single operator. The operator then removes the coupon 80 from the tensile testing apparatus and inspects the surfaces of failure, making a determination of the quality of the joint J on the basis of comparison to a base pipe failure prepared using the same template 10 and method, or on the basis of other pre-determined criteria. Thus, using the tools above described, the entire test process can be accomplished on-site by a single operator.

The template 10 and method allow efficient and precise extraction of a number of high quality tensile coupons 80 from a pipe P or from the fused joint J of a pipe P. The coupons 80 are tested to failure in a field-suitable, well controlled, self contained, tensile testing apparatus for a speedy field evaluation of the quality of the fusion joint J. The narrowing bow-tie-like pattern of the coupon 80 ensures that the failure of the coupon 80 in the tensile test will occur at the narrowest section 81 of the coupon 80. If a joint J is being tested, the narrowest cross-section 81 can be visually aligned with the joint J to ensure that it is the joint J that will be tested.

The results of the tensile test can be qualitatively compared to a sample made from the base pipe material and/or evaluated against predetermined qualitative criteria for acceptability. These qualitative criteria may be established by correlation with laboratory type tensile testing or on other reasonable bases. Such qualitative testing is not possible with known in-field destructive tests.

The material consumed by this destructive test is reasonably approximated by the length of the template 10 so, in many cases, substantially less material is consumed than in known destructive tests such as the "bend back" test.

The relief 19 of the template 10 straddles the beads B of excess molten material which was pushed out of the joint interface during the joining operation of the fusion procedure so that the narrowest cross-section of the coupon pattern 25 in the template 10 may be aligned carefully with the plane of the fusion. This ensures that the narrowest cross-section 81 of the coupon 80 is in the fused region of the pipe P.

This method and template 10 for field-testing provides quick and definitive qualitative results without imposing burdensome costs in time or material upon the operator.

Thus, it is apparent that there have been provided in accordance with the invention a method and template for producing a tensile test coupon that fully satisfy the objects, aims and advantages set forth above. While the invention has been described in conjunction with a specific embodiment thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. For producing a tensile test coupon from a plastic pipe, a method comprising the steps of:
    drilling an array of holes through a wall of the pipe, the array defining a straight-line-connectable point-to-point pattern for the coupon; and
    making straight line cuts with a reciprocating saw, the cuts connecting the array of holes in the pattern of the coupon to separate the coupon from the pipe.

2. A method according to claim 1, the holes of the coupon-defining array being arranged symmetrically in relation to a pair of intersecting axes, one axis being tangential to and the other axis being longitudinal along, an outer surface of the pipe.

3. A method according to claim 2, the holes of the coupon-defining array defining a bow-tie-like coupon symmetrical with respect to the tangential and longitudinal axes.

4. A method according to claim 3, the tangential axis lying in a plane of interface between fused sections of the pipe.

5. A method according to claim 4 further comprising the step of securing the template to the outer surface of the pipe before drilling.

6. A method according to claim 1 further comprising the steps of:

laying a template on an outer surface of the pipe, the template having an array of holes therethrough defining the straight-line-connectable point-to-point pattern for the coupon; and using the template holes to guide the drilling of the array of pattern holes through the pipe.

7. A method according to claim 6 further comprising the step of removing the template from the pipe before making the straight line cuts.

8. A method according to claim 1 further comprising the step of drilling at least two additional holes through the wall of the pipe within the pattern of the coupon, the additional holes being oriented to facilitate application of tensile force to the coupon at a narrowest cross-section of the coupon.

9. A method according to claim 8, the holes of the coupon-defining array being arranged symmetrically in relation to a pair of intersecting axes, one axis being tangential to and the other axis being longitudinal along, an outer surface of the pipe and the additional holes being aligned on the longitudinal axis and straddling the tangential axis.

10. A method according to claim 9, the holes of the coupon-defining array defining a bow-tie-like coupon symmetrical with respect to the tangential and longitudinal axes.

11. A method according to claim 10, the tangential axis lying in a plane of interface between fused sections of the pipe.

12. A method according to claim 8 further comprising the steps of:

laying a template on an outer surface of the pipe, the template having an array of holes therethrough defining the straight-line-connectable point-to-point pattern for the coupon and at least two additional holes through the wall of the pipe within the pattern of the coupon, the additional holes being oriented to facilitate application of tensile force to the coupon at a narrowest cross-section of the coupon; and using the template holes to guide the drilling of the array of pattern holes and the additional holes through the pipe.

13. A method according to claim 12 further comprising the step of securing the template to the outer surface of the pipe before drilling.

14. A method according to claim 12 further comprising the step of removing the template from the pipe before making the straight line cuts.

15. For use in producing a tensile test coupon from a plastic pipe, a template comprising:

a plate contoured for stable abutment on an outer surface of the pipe;

an array of holes through said plate, said array of holes defining a straight-line-connectable point-to-point pattern for the coupon; and at least two additional holes through said plate within said pattern of said coupon, said additional holes being oriented to facilitate application of tensile force to said coupon at a narrowest cross-section of said coupon.

16. A template according to claim 15, said holes of said coupon-defining array being arranged for symmetrical orientation in relation to a pair of intersecting axes, one said axis being tangential to and another said axis being longitudinal along, said outer surface of the pipe when said plate is in stable abutment on the pipe.

17. A template according to claim 16, said at least two additional holes being arranged for symmetrical orientation straddling said tangential axis and along said longitudinal axis.

18. A template according to claim 15, said plate having a relief for receiving beads formed on the outer surface of the pipe by fusion of the pipe along a plane of fusion interface thereof, said tangential axis lying in the plane of interface.

19. A template according to claim 18, said contour comprising a V-groove aligning said longitudinal axis of said plate with the longitudinal axis of the pipe.

20. A template according to claim 15, said holes of said coupon-defining array and said additional holes each having a hardened drill bushing.

* * * * *